United States Patent [19]
Howlett

[11] Patent Number: 5,896,853
[45] Date of Patent: Apr. 27, 1999

[54] CONTROLLED FLOW INHALERS

[75] Inventor: David Howlett, Kings Lynn, United Kingdom

[73] Assignee: Bespak plc, Norfolk, United Kingdom

[21] Appl. No.: 08/847,390

[22] Filed: Apr. 24, 1997

[30] Foreign Application Priority Data

Apr. 26, 1996 [GB] United Kingdom .................. 9608708

[51] Int. Cl.$^6$ .................. A61M 15/00; A61M 16/10; F16K 11/00; G05D 11/02
[52] U.S. Cl. .................. 128/200.23; 128/203.12; 128/203.24; 128/207.16
[58] Field of Search .................. 128/200.23, 200.14, 128/203.12, 203.24, 207.16

[56] References Cited

U.S. PATENT DOCUMENTS

| | | | |
|---|---|---|---|
| 3,826,413 | 7/1974 | Warren | 128/200.23 |
| 4,534,343 | 8/1985 | Nowacki et al. | 128/200.23 |
| 4,592,348 | 6/1986 | Waters, IV et al. | |
| 5,040,527 | 8/1991 | Larson et al. | 128/200.23 |
| 5,447,150 | 9/1995 | Bacon | 128/200.23 |
| 5,522,380 | 6/1996 | Dwork | 128/200.23 |
| 5,598,836 | 2/1997 | Larson et al. | 128/200.23 |
| 5,617,844 | 4/1997 | King | 128/200.23 |
| 5,655,520 | 8/1997 | Howe et al. | 128/205.24 |

FOREIGN PATENT DOCUMENTS

WO92/09323  6/1992  WIPO.

Primary Examiner—Kimberly L. Asher
Attorney, Agent, or Firm—Beveridge, DeGrandi, Weilacher & Young, LLP

[57] ABSTRACT

The invention relates to an inhaler for products such as medicaments, and particularly to an inhaler for transferring to a patient, at a controlled air flow, a metered dose of a medicament contained in a pressurised dispensing container. The inhaler includes a housing adapted to receive a pressurised dispensing container, a mouthpiece, a duct connecting the container outlet with the mouthpiece, and an air inlet arrangement having at least one air inlet for allowing air into the inhaler when a user applies suction to the mouthpiece. The air inlet arrangement also has an air flow controller in which a piston member with a tapering external surface is movable due to a pressure change when suction is applied to the mouthpiece. The resulting piston movement effects a change in the flow of air through the air inlet. The air flow controller also includes a spring for urging the piston member to a rest position to allow maximum air flow to the air inlet. The piston member is movable axially against the action of the spring within the air inlet due to the pressure change, whereby a gap between the external surface of the piston member and the air inlet is increasingly reduced as the piston member moves further into the air inlet.

4 Claims, 3 Drawing Sheets 5,896,853

1

CONTROLLED FLOW INHALERS

BACKGROUND

The invention relates to an inhaler for products such as medicaments and particularly to an inhaler for transferring to a patient at a controlled air flow a metered dose of a medicament contained in a pressurised dispensing container.

In known metered dose inhalers, the aerosol stream from a pressurised dispensing container is fired towards a patient or user of the inhaler into a air flow travelling in the same direction. In known devices, a user inhales through a mouth piece of the inhaler and creates an air flow through the container from air inlet holes which are generally at a part of the inhaler well spaced from the mouth piece. The medicament is then released into this air flow at a point between the air inlet holes and the mouth piece so that it is travelling in the same direction as the air flow. Typically in such devices, there is no restriction in the air flow between the air inlet holes and the mouth piece. Because of this, a substantial air flow may be created by a user of the device and, because the medicament is fired into the air flow in the same direction as the air flow, the effect is that particles of medicament can attain quite substantial velocities. As inhalers of this type are normally designed to be as small as practical for the convenience of users, the distance between the point at which the medicament is fired into the air flow and the patients mouth is usually quite small so that there is little distance to reduce the inertia of the particles of medicament with the result that the particles may impact in the oro-pharynx of a user with quite high velocity. This can be a problem with some medicaments.

In an effort to overcome this problem, devices have been produced in which the medicament is fired into a holding volume which allows the velocity of the medicament to be reduced and also allows some evaporation to occur.

However, these devices with a holding volume tend to be of significantly larger size than the standard metered dose inhalers and therefore less convenient and attractive to users.

GB-A-2279879 describes an inhaler which has air inlets for allowing air into the inhaler when a user applies suction to the mouth piece. The air inlets are provided at a location axially between the air outlet of the duct means from the product container to the mouth piece, and the mouth piece, and passages are provided connecting the air inlet to a location adjacent the outlet of the duct means. In use, when a user inhales through the mouth piece, an air flow is created from the air inlet to the mouth piece, the air flow having a component directed away from the mouth piece towards the outlet of the duct means.

Such an inhaler thus allows delivery of medicament to a user at reduced velocity without significantly increasing the size of the inhaler.

Another solution to the problem would be to control the rate of air flow and the particles entrained therein.

SUMMARY OF THE INVENTION

It is an object of the present invention to provide an inhaler, wherein a controlled air flow is achieved of a predetermined rate regardless of patient respiratory effort.

The invention therefore provides an inhaler for dispensing a product comprising a housing adapted to receive a pressurised dispensing container, a mouth piece, duct means connecting an outlet of the container with the mouth piece, air inlet means having at least one air inlet for allowing air into the inhaler when a user applies suction to the mouth piece, the air inlet means further comprising an air flow controller having a piston member having a tapered external surface which is movable due to a pressure change when suction is applied to the mouth piece, the resulting movement effecting a change in the flow of air through the air inlet, the air flow controller further comprising spring means for urging the piston member into a rest position to allow maximum air flow to the air inlet, the piston member being movable axially against the action of the spring within the air inlet due to the pressure change, such that a gap between the external surface of the piston member and the air inlet is increasingly reduced as the piston member moves further into the air inlet.

A preferred embodiment of the invention will now be described, by way of example only, with reference to the accompanying drawings in which:

DETAILED DESCRIPTION

Figure 1:
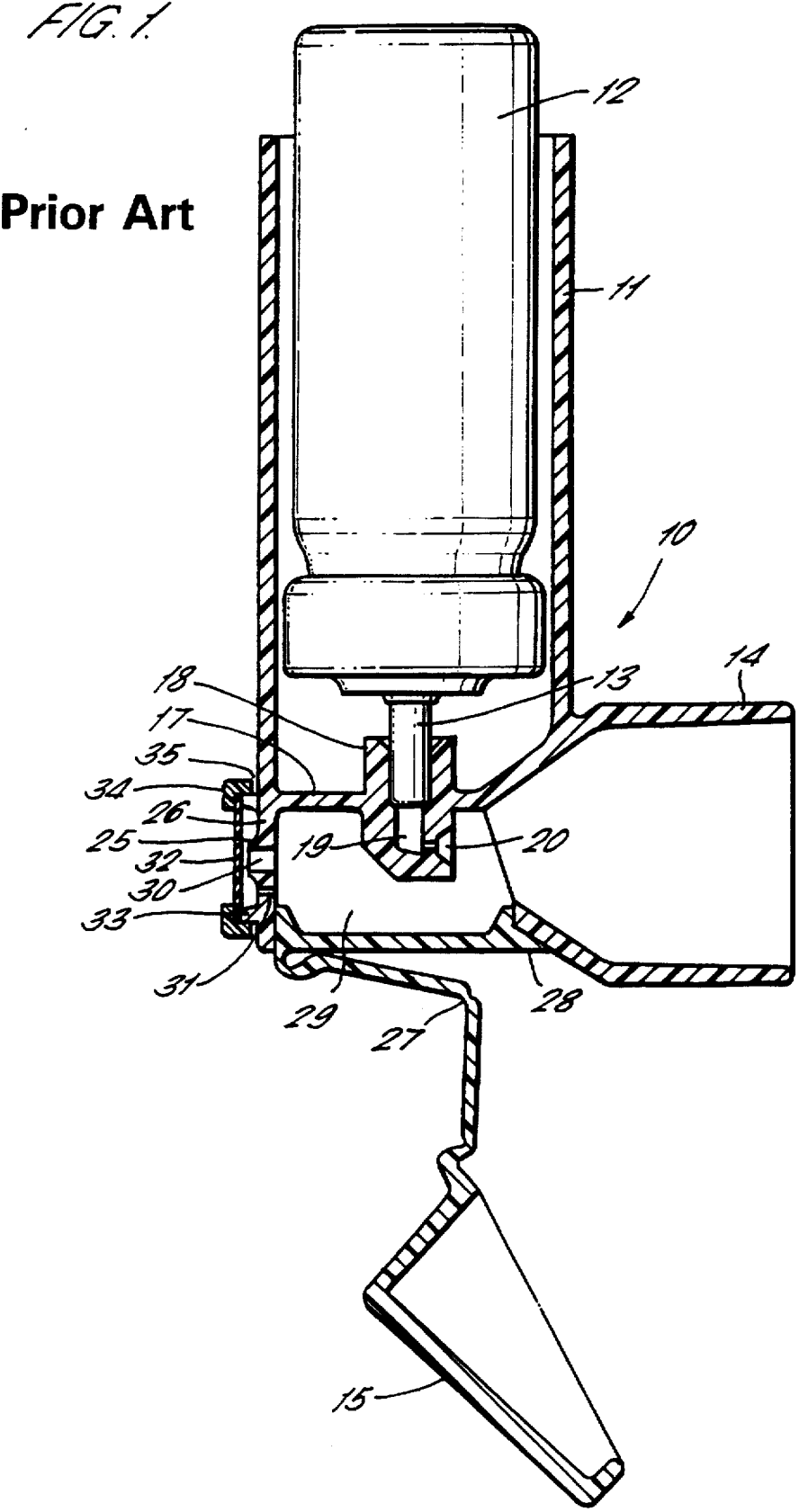
FIG. 1 is a cross-sectional side elevation through an inhaler according to the prior art.
Figure 2:
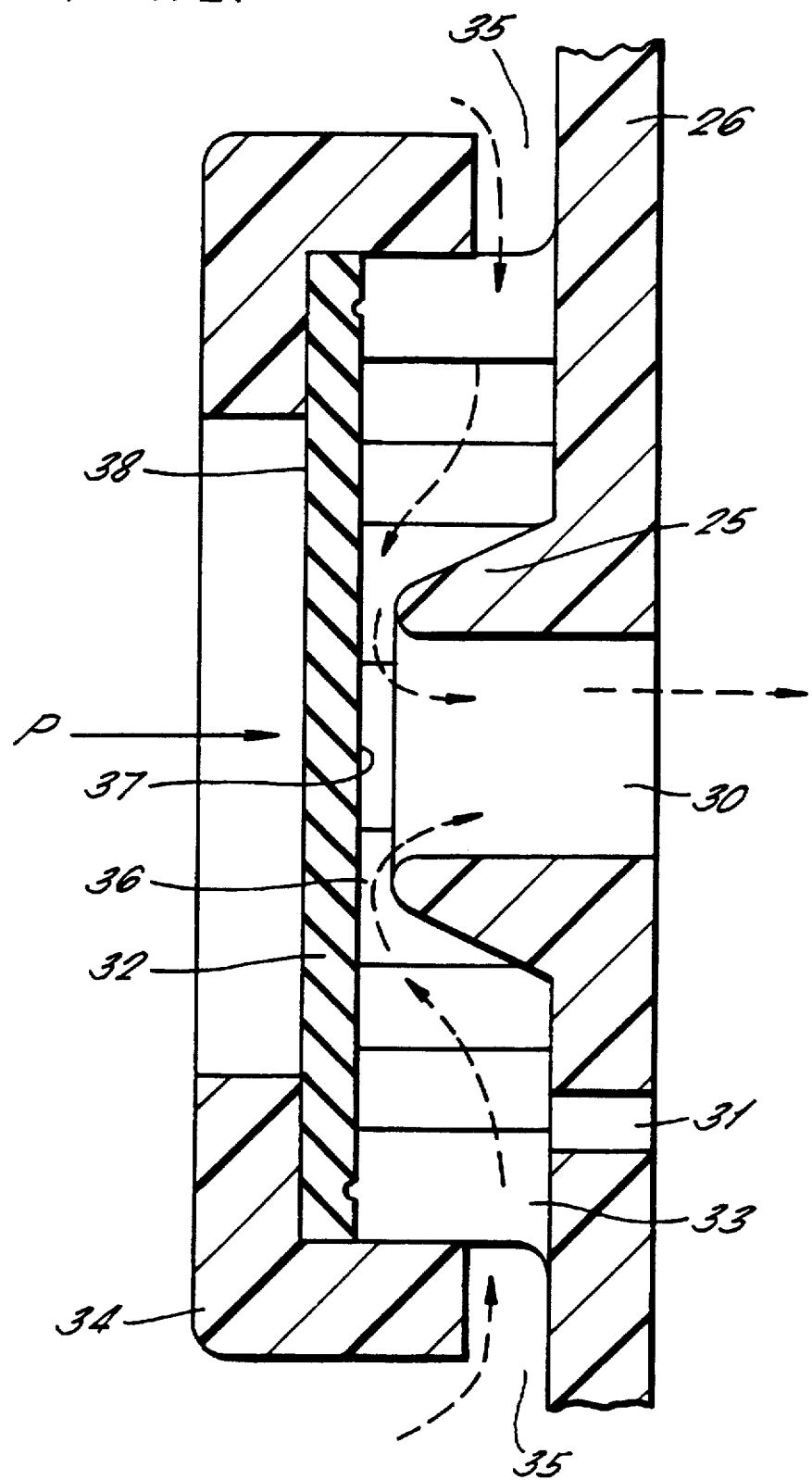
FIG. 2 is an enlarged cross section of the diaphragm arrangement of the inhaler of FIG. 1.

Referring to FIGS. 1 and 2, an inhaler 10 for a product such as a medicament comprises a housing 11 for receiving a pressurised dispensing container 12 of medicament, a mouth piece 14 for insertion into the mouth of a user of the inhaler, and a cover 15 for the mouth piece 14.

The container housing 11 is generally cylindrical and open at its upper end. A lower wall 17 of the housing 11 includes an annular socket 18 for receiving the tubular valve stem 13 of the container 12. The socket 18 communicates via a duct 19 ending in an orifice 20 with the mouth piece 14.

The mouth piece 14 which may be generally circular or shaped to fit the mouth and is connected to or forms a part of the housing 11.

The cover 15 of the device, which fits over the open mouth piece 14, is connected by a flexible hinge portion 27 to a cover attachment 28 which fits in the lower part of the housing 11 to attach the cover 15 to the housing 11.

All of the components of the inhaler 10 may be plastics mouldings.

It will be appreciated that the lower wall formation 17 of housing 11 forms a barrier between the open end of the housing 11 and the mouth piece 14 so that there is no air flow passage from around the container 12 to the mouth piece 14.

A chamber 29 is formed in the lower part of the housing 11, below the lower formation wall 17, to which the mouth piece 14 is joined. In the rear wall 26 of the chamber 29, i.e. the wall furthest from the adjoining mouth piece 14, there is an orifice forming a primary air inlet 30 and a bleed port forming a secondary air inlet 31, both of which inlets 30, 31 communicate with the chamber 29. The primary air inlet 30 is at least partly defined by a raised annulus 25 on the rear wall 26 of the housing 11. Attached to the rear wall 26, extending over the primary and secondary air inlets 30 and 31, is a flexible elastomeric diaphragm 32 mounted on a support 33 and held in position by a retainer 34. The relative dimensions of the support 33 and annulus 25 are such that the diaphragm 32 is held, at rest, with a gap 36 between the diaphragm 32 and the mouth of the primary air inlet orifice 30. The support 33 also defines a plurality of tertiary air inlets 35.

In use, a patient or user holds the inhaler 10, usually in one hand, and applies his mouth to the mouth piece 14. The user then inhales through the mouth piece 14 and this creates an air flow from the tertiary air inlets 35 via the primary and secondary air inlets 30 and 31 into the chamber 29 (as shown by the broken arrows in FIG. 2) to the mouth piece 14.

Once the user has started inhaling through the mouth piece 14, the suction causes the pressure on the inside surface 37 of the diaphragm 32 to drop relative to the pressure P on the external surface 38. As a result the diaphragm 32 distorts towards the mouth of the primary air inlet 30 thereby reducing, and possibly closing, the gap 36 and restricting the air flow through the primary air inlet 30. If the gap 36 is closed completely, some air will continue to enter the chamber 29 via the secondary air inlet 31.

After the user has started inhaling through the mouth piece 14, the container 12 is depressed downwardly on to its stem 13 to release a dose of medicament from the container. The dose of medicament is projected by the pressure in the container 12 via the duct 19 and through the orifice 20 and then mixes with the turbulent air flow in the chamber 29 and thence is inhaled by the user.

The air flow can thus be controlled to ensure that the velocity of medicament particles is relatively low when they enter the oro-pharynx region of the patient regardless of the patient respiratory effort. Preferably the air flow is controlled at 30 to 60 litres per minute and this can be achieved by a specific combination of diaphragm flexibility, the diameter of the air inlet 31 and the size of the gap 36.

Figure 3:
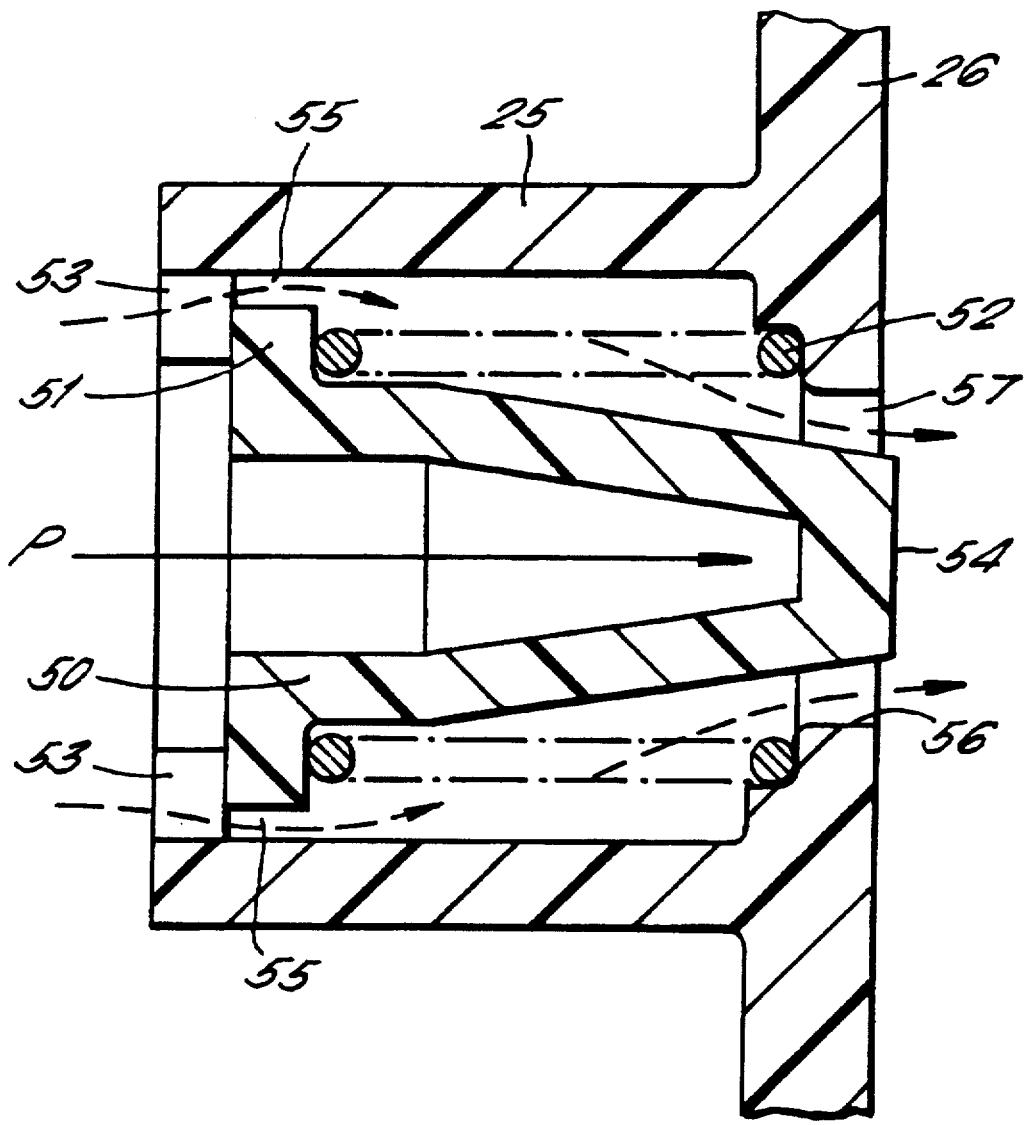
FIG. 3 is an enlarged cross-sections of the air flow controller of the inhaler of the present invention.

In FIG. 3, an air flow controlling device according to the present invention is illustrated. The deformable elastomeric components are replaced by a more rigid piston-like component 50 of a frusto-conical construction which is located inside the annulus 25. At one end, the component 50 has a radially extending flange 51 which is urged, by a return spring 52, into contact with stop means 53 on the inner surface of the annulus 25. The tertiary air inlets 55 are located around the stop means 53 and the primary air inlet 56 is an orifice in the rear wall 26 of the chamber 29. The other end of the component 50 is located in the primary air inlet 56 surrounded by an annular gap 57.

As the user inhales, the resulting pressure drop on the underside 54 of the component 50 causes the relatively higher pressure P on the other surface to move the component 50 against the bias of the spring 52 further into the primary air inlet 56. As the component 50 moves further within the primary air inlet 56, the gap 57 reduces thereby restricting the air flow into the chamber 29. The need for a secondary air inlet may be obviated if the spring characteristics are selected or further stop means installed such that the component 50 is not allowed to move far enough within the primary air inlet 56 to close the gap 57 completely. Otherwise a secondary air inlet may be provided in the form of an orifice in the base of the component 50 or in another appropriate location.

I claim:

1. An inhaler for dispensing a product comprising a housing adapted to receive a pressurised dispensing container, a mouth piece, duct means connecting an outlet of the container with the mouth piece, air inlet means having at least one air inlet for allowing air into the inhaler when a user applies suction to the mouth piece, the air inlet means further comprising an air flow controller having a piston member having a tapering external surface which is movable due to a pressure change when suction is applied to the mouth piece, the resulting movement effecting a change in the flow of air through the air inlet, the air flow controller further comprising spring means for urging the piston member into a rest position to allow maximum air flow to the air inlet, the spring within the air inlet due to the pressure change, such that a gap between the external surface of the piston member and the air inlet is increasingly reduce as the piston member moves further into the air inlet.

2. An inhaler as claimed in claim 1 in which the air inlet means further comprise at least one secondary air inlet for allowing air into the inhaler, the flow of air through which is not affected by the air flow controller.

3. An inhaler as claimed in claim 1 in which the air inlet means further comprise at least one tertiary air inlet for allowing air into the air flow controller, which is located on an external surface of the inhaler housing.

4. An inhaler as claimed in claim 1 in which the air flow into the inhaler is controlled at a rate in the range 30 to 60 litres per minute.

* * * * *